US010524949B2

(12) United States Patent
Mason et al.

(10) Patent No.: US 10,524,949 B2
(45) Date of Patent: Jan. 7, 2020

(54) KNEE BRACE WITH ADJUSTABLE STRUT LENGTH AND DYNAMIC STRUT LENGTHENING

(71) Applicant: United Surgical Associates, Inc., Solvang, CA (US)

(72) Inventors: Jeffrey T. Mason, Escondido, CA (US); Russell S. Moir, Solvang, CA (US); Bryan K. Bowman, Roann, IN (US)

(73) Assignee: United Surgical Associates, Inc., Solvang, CA (US)

( * ) Notice: Subject to any disclaimer, the term of this patent is extended or adjusted under 35 U.S.C. 154(b) by 973 days.

(21) Appl. No.: 14/818,587

(22) Filed: Aug. 5, 2015

(65) Prior Publication Data

US 2016/0038327 A1      Feb. 11, 2016

Related U.S. Application Data

(60) Provisional application No. 62/033,553, filed on Aug. 5, 2014.

(51) Int. Cl.
    *A61F 5/01*            (2006.01)

(52) U.S. Cl.
CPC .... *A61F 5/0123* (2013.01); *A61F 2005/0137* (2013.01); *A61F 2005/0139* (2013.01);
(Continued)

(58) Field of Classification Search
CPC .... A61F 5/0123; A61F 5/0125; A61F 5/0106; A61F 2005/0132; A61F 2005/0134; A61F 2005/0137; A61F 2005/0139; A61F 2005/0141; A61F 2005/0144; A61F 2005/0148; A61F 2005/0155; A61F 2005/0167; A61F 2005/0165; A61F 2005/0172; A61F 2005/0174; A61F 5/01; A61F 5/0102; A61F 5/0104; A61F 5/0109; A61F 2005/0146; A61F 2005/0153; A61F 2005/0169; A61F 5/0111; A61F 5/0113; A61F 5/0127; A61F 5/0193; A61F 5/0118; A61F 5/013; A61G 13/123

See application file for complete search history.

(56) References Cited

U.S. PATENT DOCUMENTS 3,826,251 A * 7/1974 Ross ...................... A61F 2/646
                                                                                              602/16
4,428,369 A * 1/1984 Peckham .............. A61F 5/0123
                                                                                              602/16

(Continued)

*Primary Examiner* — Ophelia A Hawthorne
*Assistant Examiner* — Rachel A Berezik
(74) *Attorney, Agent, or Firm* — Felix L. Fischer

(57) ABSTRACT

A knee brace incorporates an upper attachment assembly having an upper cuff with medial and lateral struts extending therefrom and a lower attachment assembly having a lower cuff with lower medial and lateral struts extending therefrom. The upper and lower medial struts are connected proximate a user's knee by a medial hinge assembly and the upper and lower lateral struts are connected proximate the user's knee by a lateral hinge assembly. At least one of the struts includes a mechanism dynamically extending the strut with respect to a rotation point of that strut in the associated hinge upon flexion of the upper and lower attachment assemblies between a flexed position and an extended position.

11 Claims, 18 Drawing Sheets

(52) U.S. Cl.
CPC .......... *A61F 2005/0146* (2013.01); *A61F 2005/0174* (2013.01)

(56) References Cited

U.S. PATENT DOCUMENTS

| | | | | |
|---|---|---|---|---|
| 4,886,054 A | * | 12/1989 | Castillo | A61F 5/0123 602/26 |
| 5,547,464 A | * | 8/1996 | Luttrell | A61F 5/0111 482/111 |
| 5,938,629 A | * | 8/1999 | Bloedau | A61F 5/0125 602/16 |
| 6,309,368 B1 | * | 10/2001 | Herzberg | A61F 5/0123 602/16 |
| 6,375,632 B1 | * | 4/2002 | Albrecht | A61F 5/0125 602/16 |
| 2003/0149386 A1 | * | 8/2003 | Ceriani | A61F 5/0123 602/26 |
| 2005/0234376 A1 | * | 10/2005 | Rossi | A61F 5/0125 602/16 |
| 2006/0155229 A1 | * | 7/2006 | Ceriani | A61F 5/0125 602/16 |
| 2006/0206045 A1 | * | 9/2006 | Townsend | A61F 5/0125 602/26 |
| 2013/0296754 A1 | * | 11/2013 | Campbell | A61F 5/0123 602/16 |

* cited by examiner

KNEE BRACE WITH ADJUSTABLE STRUT LENGTH AND DYNAMIC STRUT LENGTHENING

REFERENCES TO RELATED APPLICATIONS

This application claims priority of U.S. provisional application Ser. No. 62/033,553 filed on Aug. 5, 2014 having a common assignee with the present application, the disclosure of which is incorporated herein.

BACKGROUND INFORMATION

Field

Embodiments of the disclosure relate generally to the field of anatomical support braces and more particularly to a system for orthopedic knee braces for altering strut length over a range of knee flexure from a flexed to extended position to induce lateral loading on the knee.

Background

Certain conditions including osteo arthritis may be treated with appropriate anatomical support braces. This is particularly true of the knee. However, a primary element of providing relief in the case of osteo arthritis is the necessity for asymmetrically unloading the knee joint in the extended position or changing the medial/lateral angle between the thigh and calf of the leg between the flexed and extended positions. This complex motion has been attempted in prior art braces. However, the mechanisms have proved to be complex, costly and not particularly amenable to adjustment.

It is therefore desirable to provide a strut system orthopedic braces which provides and increasing or decreasing strut length from a flexed position to an extended position. It is also desirable to provide adjustment for the strut length to achieve variable side loading or angular change.

SUMMARY

Embodiments disclosed herein provide a knee brace having an upper attachment assembly having an upper cuff with medial and lateral struts extending therefrom and a lower attachment assembly having a lower cuff with lower medial and lateral struts extending therefrom. The upper and lower medial struts are connected proximate a user's knee by a medial hinge assembly and the upper and lower lateral struts are connected proximate the user's knee by a lateral hinge assembly. At least one of the struts includes a mechanism dynamically extending the strut with respect to a rotation point of that strut in the associated hinge upon flexion of the upper and lower attachment assemblies between a flexed position and an extended position.

The features, functions, and advantages that have been discussed can be achieved independently in various embodiments of the present disclosure or may be combined in yet other embodiments further details of which can be seen with reference to the following description and drawings.

DETAILED DESCRIPTION

Embodiments disclosed herein provide a knee brace which incorporates a dynamic strut on one side of the brace that changes length as the brace changes flexion angle. In alternative embodiments the dynamic strut may either extend or contract. A second embodiment includes a manually adjustable dynamic strut on one side of the brace which adjusts the amount that the strut changes in length as the brace changes flexion angle. A third embodiment provides an adjustable strut on one side of the brace that manually changes the length of the strut but does not change with flexion angle. A forth embodiment provides a combination with both a manually adjustable strut on one side of the brace and a nonadjustable dynamic strut on the other side. A fifth embodiment provides a combination with a manually adjustable strut on one side of the brace and a manually adjustable dynamic strut on the other.

Figure 1:
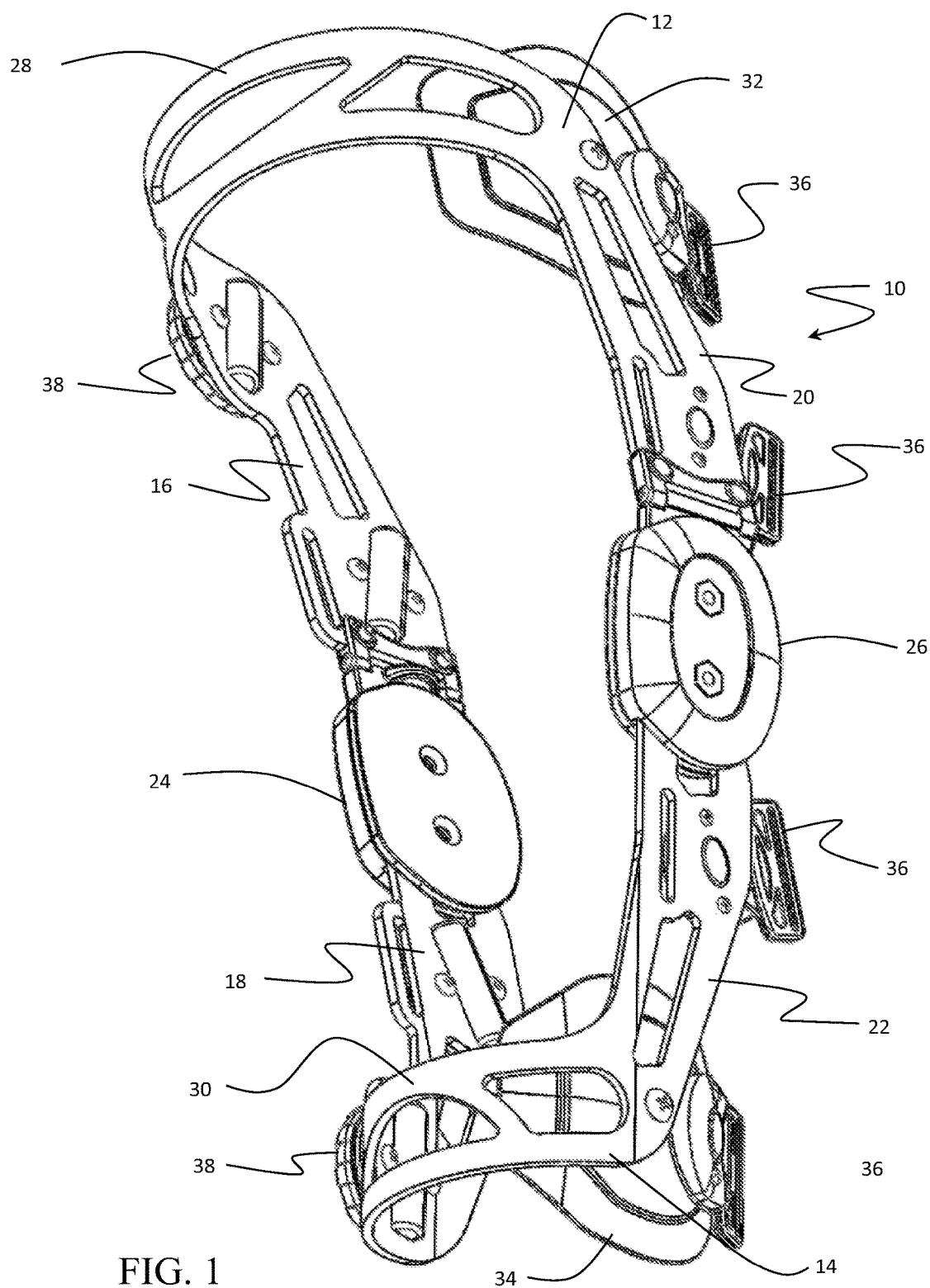
FIG. 1 is a pictorial view of an exemplary embodiment of a knee brace having dynamic lengthening of a medial strut upon motion of the brace from a flexed to extended position.

Referring to the drawings, FIG. 1 an example orthopedic knee brace 10 is composed of an upper attachment assembly 12 to be received on the thigh of the patient and a lower attachment assembly 14 to be received on the lower leg of the patient. The brace 10 includes an upper lateral strut 16 and a lower lateral strut 18 and an upper medial strut 20 and lower medial strut 22. Hinge assemblies 24 and 26 interconnect the upper and lower lateral and medial struts, respectively. The upper attachment assembly 12 includes an anterior arch support or cuff 28 extending between the upper lateral strut 16 and upper medial strut 20, engaging the user's anterior surface of the users thigh, positioning the substantially rigid upper lateral strut 16 and upper medial strut 20 to extend down the leg to meet the hinge assemblies substantially at the user's knee. The lower attachment assembly 14 also includes an anterior arch support or cuff 30 extending between the lower lateral strut 18 and the lower medial strut 20, which engages the shin or anterior portion of the user's lower leg positioning the substantially rigid lower lateral strut 18 and lower medial strut 22 to extend up the leg to meet the hinge assemblies substantially at the user's knee. The upper attachment assembly 12 includes an upper engagement pad 32, sometimes referred to as a "wing" or "paddle", which contacts the medial surface of the user's thigh. The lower attachment assembly 14 includes a lower engagement pad 34 which contacts the medial surface of the user's lower leg. Strap engagement elements 36 and tensioning mechanisms 38 are employed at various locations on the struts to affix the brace 10 to the users legs. Example elements and mechanisms for this application may be as disclosed in application Ser. No. 61/860,215 entitled Orthopedic Brace Securing and Tensioning System having a common assignee with the present application, the disclosure of which is incorporated herein by reference.

Figure 2:
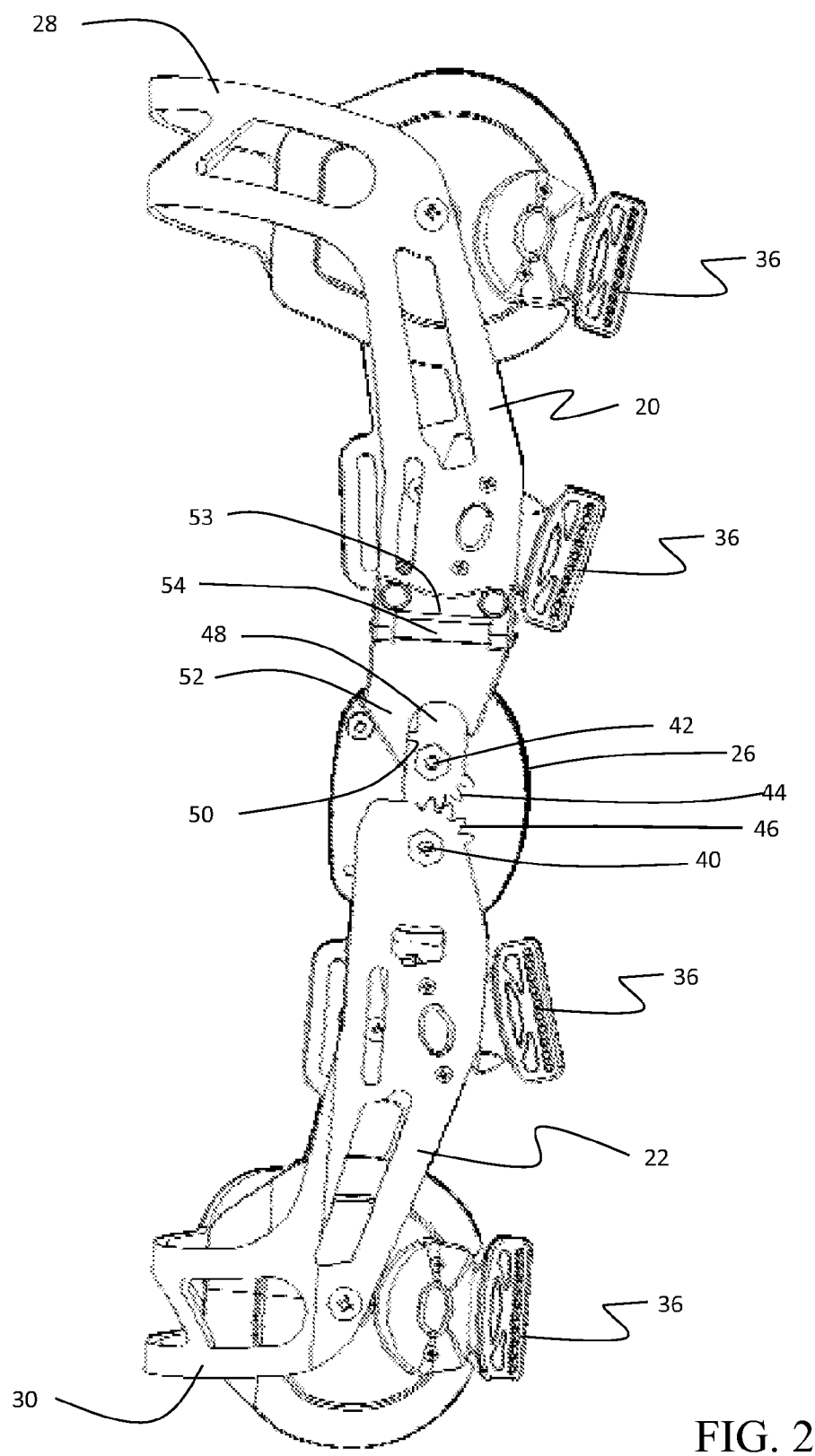
FIG. 2 is a side view of the medial struts of the embodiment of FIG. 1.

FIG. 2 shows the upper medial strut 20 and lower medial strut 22 as engaged at the hinge 26. The cover plate of the hinge has been removed showing the details of the engagement. For an exemplary embodiment, the medial side of the brace 10 incorporates the dynamic strut for creating the unloading condition for the knee. The lower medial strut 22 is engaged in the hinge at a pivot pin 40 providing a point about which the strut rotates. The upper medial strut 20 is similarly engaged by a pivot pin 42 providing a point about which the upper strut rotates. Engaging teeth 44 on a periphery of the upper medial strut 20 and engaging teeth 46 on a mating periphery of the lower medial strut 22 interengage to coordinate the rotation of the struts in the hinge. The mechanism for dynamic extension of the strut is provided by a buck 48 secured to the pivot pin 42 and received in a channel 50 in a saddle 52, the operation of which will be described in greater detail subsequently, the buck sliding in channel 50 relative to the saddle to increase and decrease the overall length of the upper medial strut 20 as the upper and lower medial struts are rotated from flexed to extended. The saddle 52 is secured to an interface 53 in the upper medial strut 20 with a hinge 54 to allow lateral angular variation between the upper medial strut 20 and lower medial strut 22.

Figure 3:
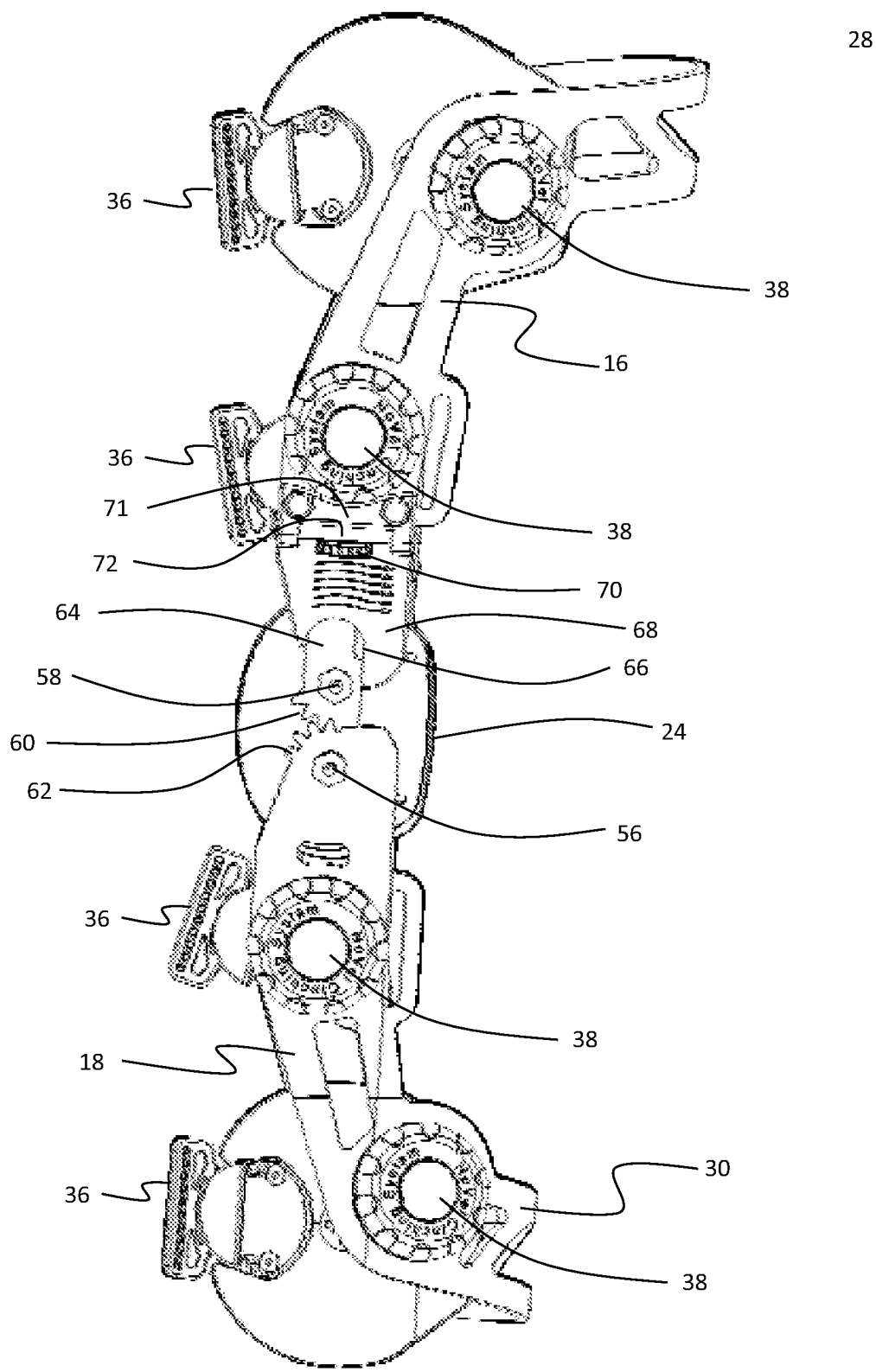
FIG. 3 is a side view of the lateral struts of the embodiment of FIG. 1.

As shown in FIG. 3, the upper lateral strut 16 and lower lateral strut 18 engage at the hinge 24. The cover plate of the hinge has been removed showing the details of the engagement. For an exemplary embodiment, the lateral side of the brace 10 incorporates the manually adjustable strut to adjust the unloading condition for the knee by changing the length of the strut relative to the medial strut but without changing in length through the angular flexion and extension of the brace. The lower lateral strut 18 is engaged in the hinge at a pivot pin 56 about which the strut rotates. The upper lateral strut 16 is similarly engaged by a pivot pin 58 about which the upper strut rotates. Engaging teeth 60 on a periphery of the upper lateral strut 16 and engaging teeth 62 on a mating periphery of the lower lateral strut 18 interengage to coordinate the rotation of the struts in the hinge. The mechanism for adjustment of the strut length is provided by a buck 64 secured to the pivot pin 58 and received in a channel 66 in a saddle 68, the operation of which will be described in greater detail subsequently, the buck sliding in channel 66 relative to the saddle to increase or decrease the length of the upper lateral strut as controlled by an adjustment wheel 70. The saddle 68 is secured to an interface 71 on the strut 16 with a hinge 72 to allow lateral angular variation between the upper lateral strut 16 and lower lateral strut 18.

Figure 4A:
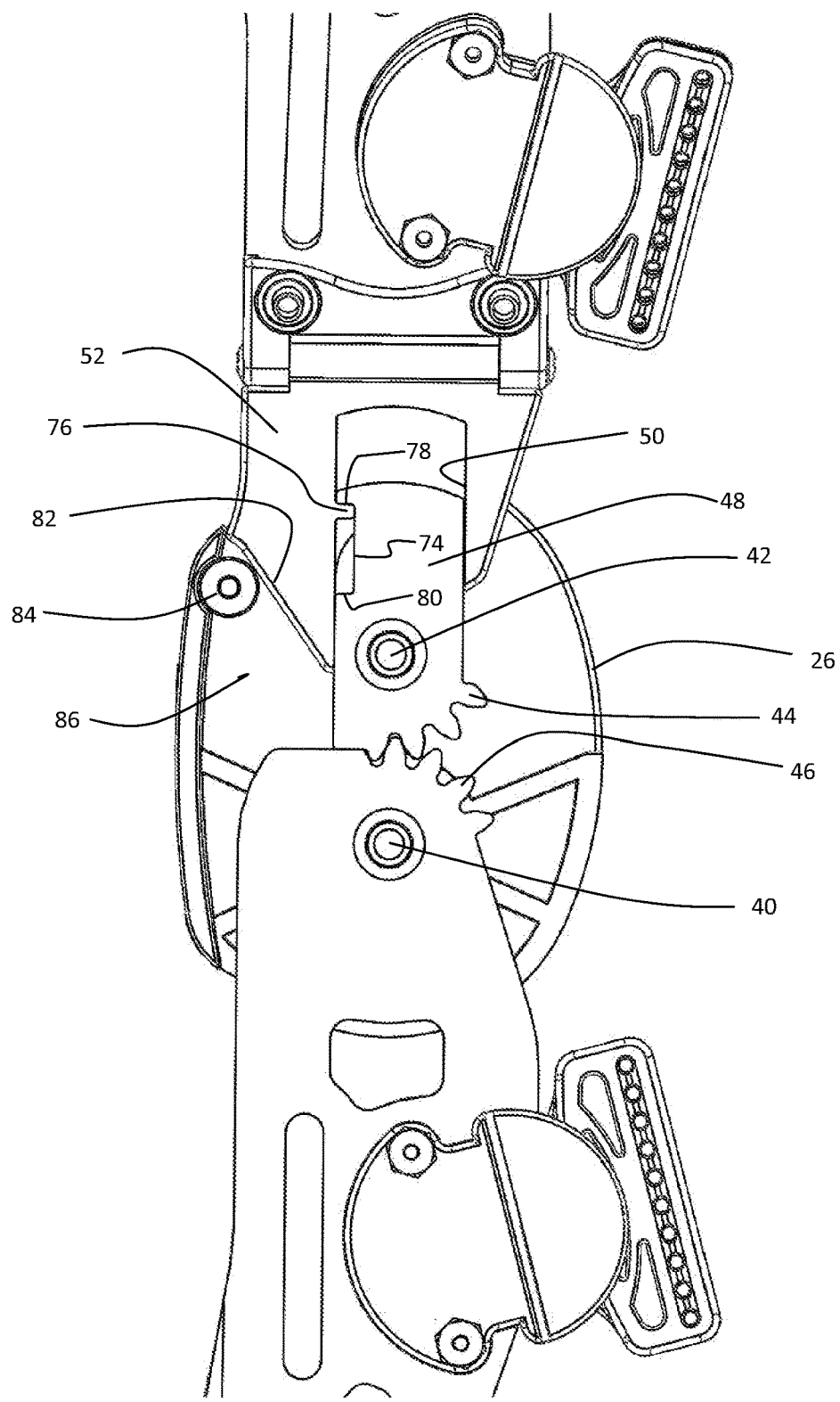
FIG. 4A is a detailed side view of a dynamic extension mechanism in an upper medial strut of the embodiment.

The elements for operation of the dynamically extending strut are shown in detail in FIGS. 4A-4D. As shown in FIG. 4A, the buck 48 includes a relief 74 in which a stop pin 76, protruding from the saddle 52, is received. Travel of the buck 48 within the channel 50 is limited by engagement of the stop pin 76 at upper termination 78 and lower termination 80. Lengthening of the strut in the fully extended position of the brace is caused by engagement of a ramp 82 on the lower periphery of the saddle 52 with a pinned roller 84 secured to the cover 86 of the hinge 26 offset from the rotation point established by the pivot pin 42. Relative location of the roller 84 and pivot pin 42 determine the angle of flexion at which the roller contacts the ramp.

Figure 4B:
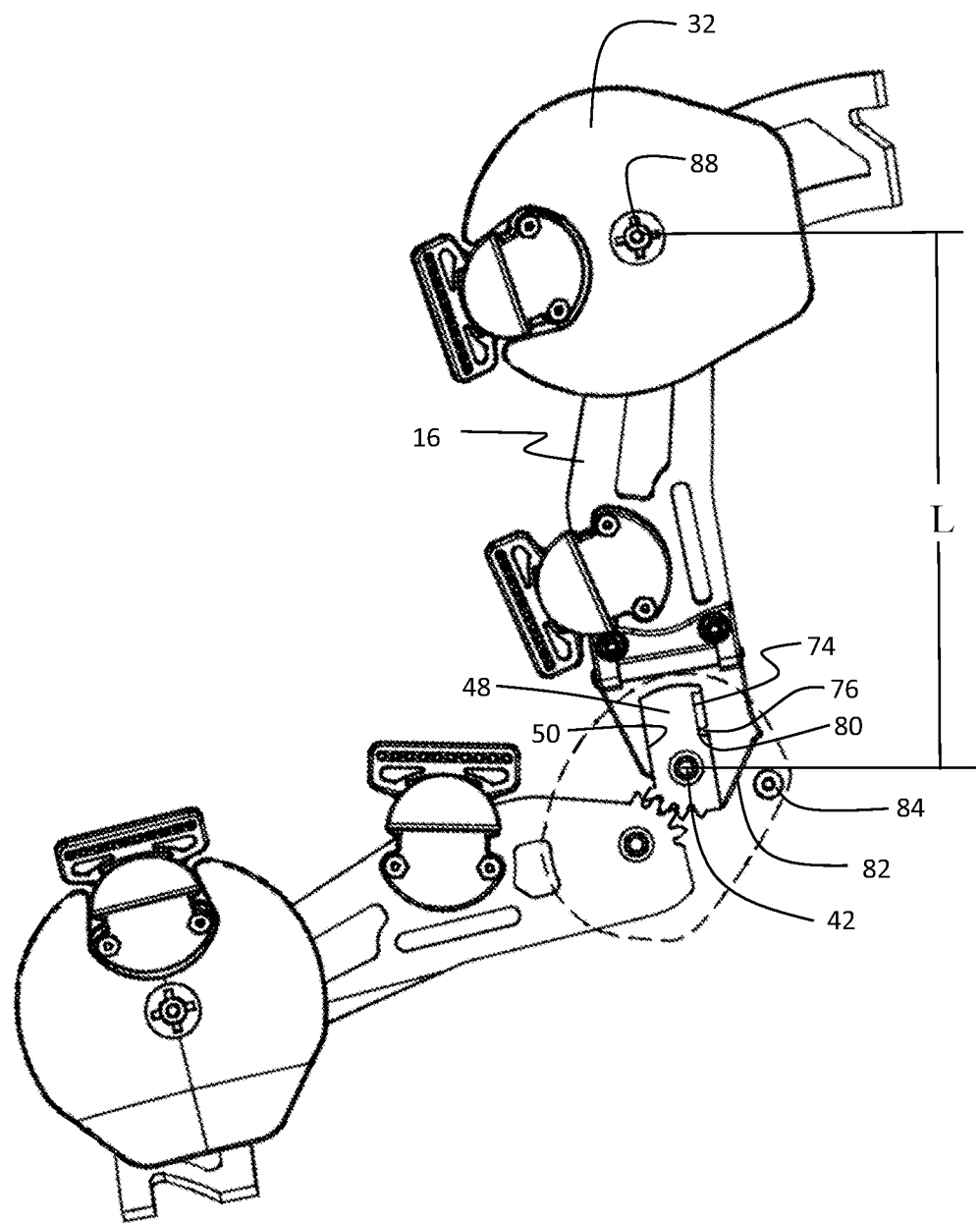
FIG. 4B is a side view of the medial struts of the brace in a flexed position of the leg.
Figure 4C:
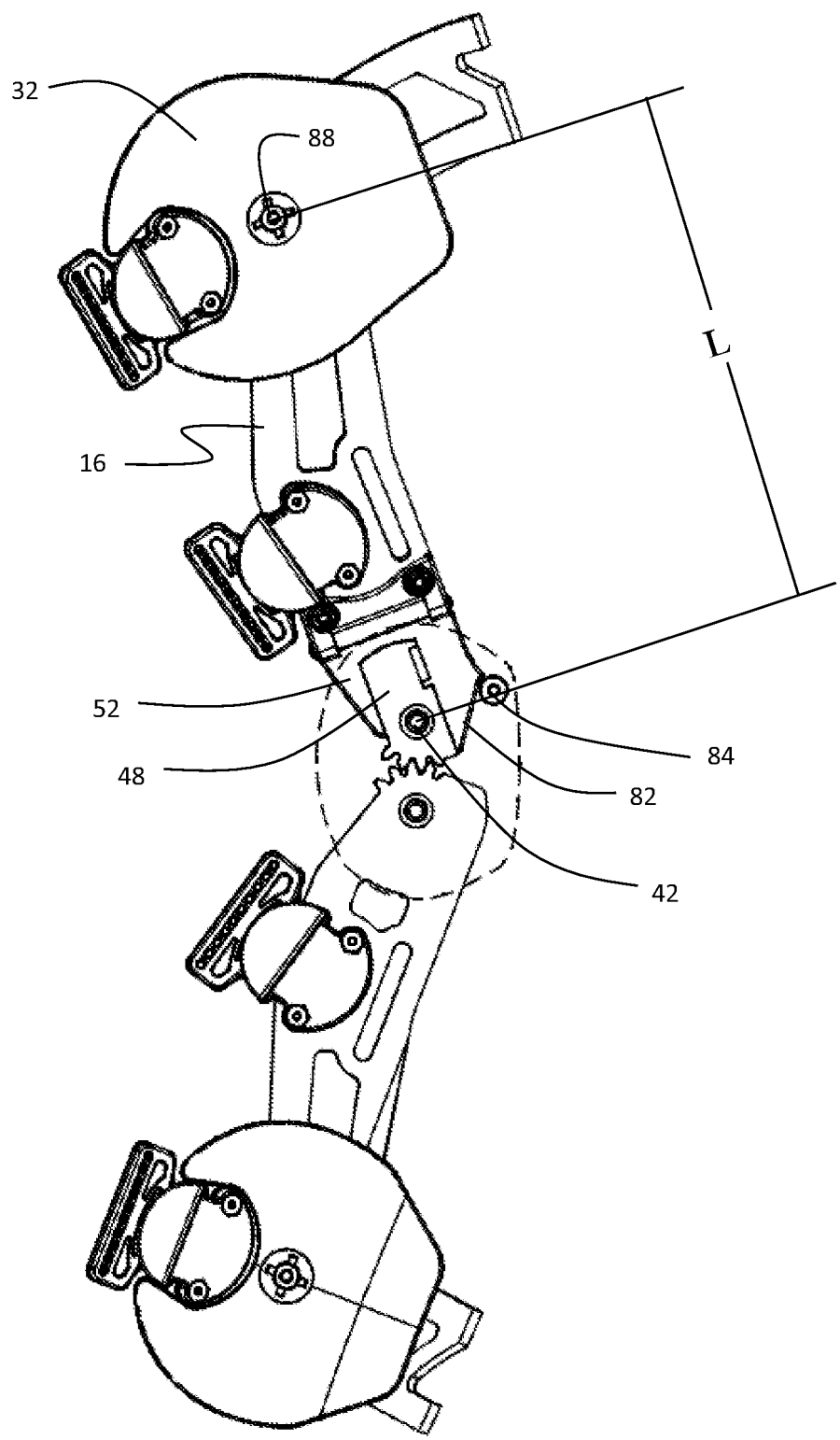
FIG. 4C is a side view of the medial struts of the brace in a first partially extended position of the leg prior to commencement of dynamic extension.
Figure 4D:
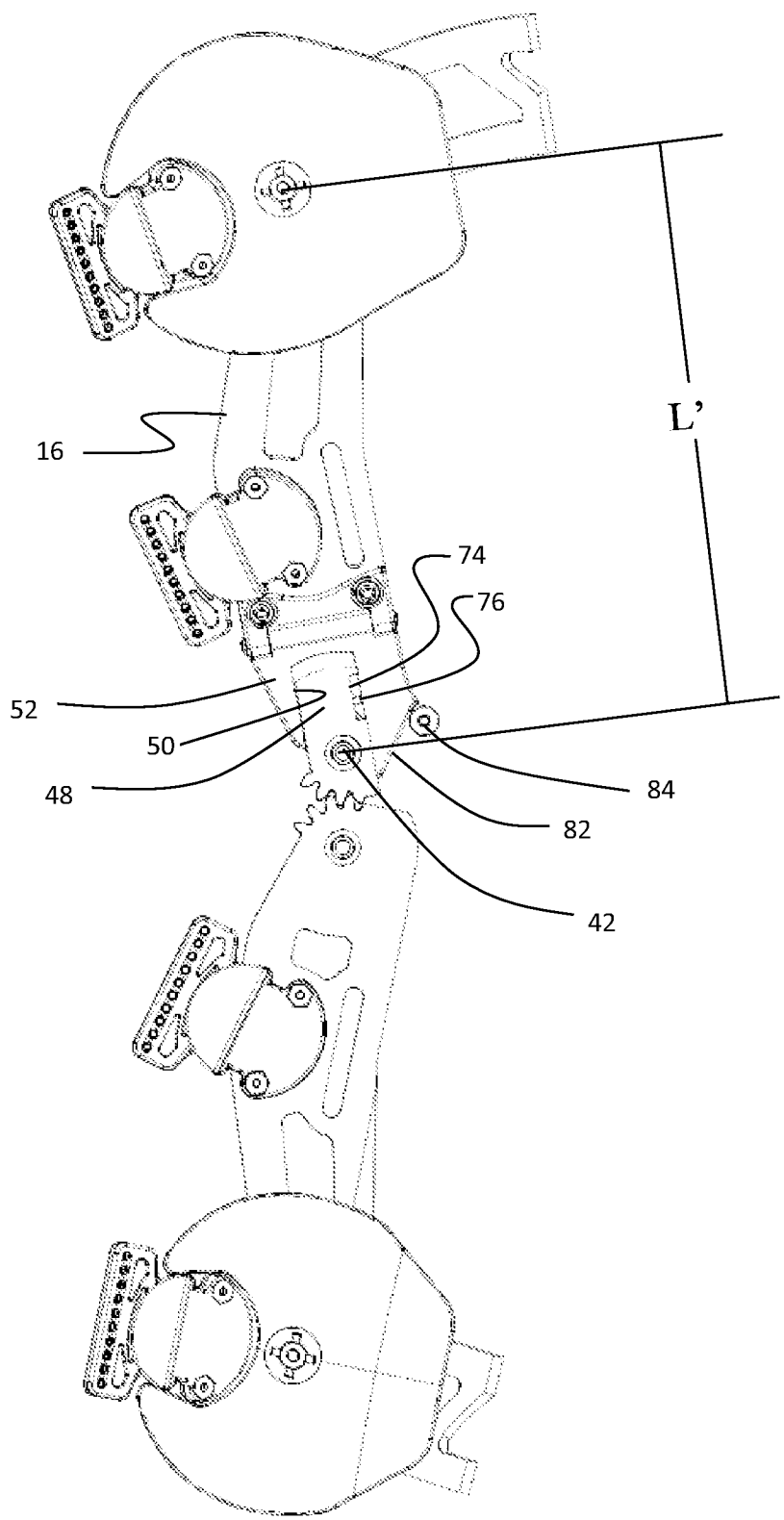
FIG. 4D is a side view of the medial struts of the brace in a second partially extended position of the leg during dynamic extension.
Figure 4E:
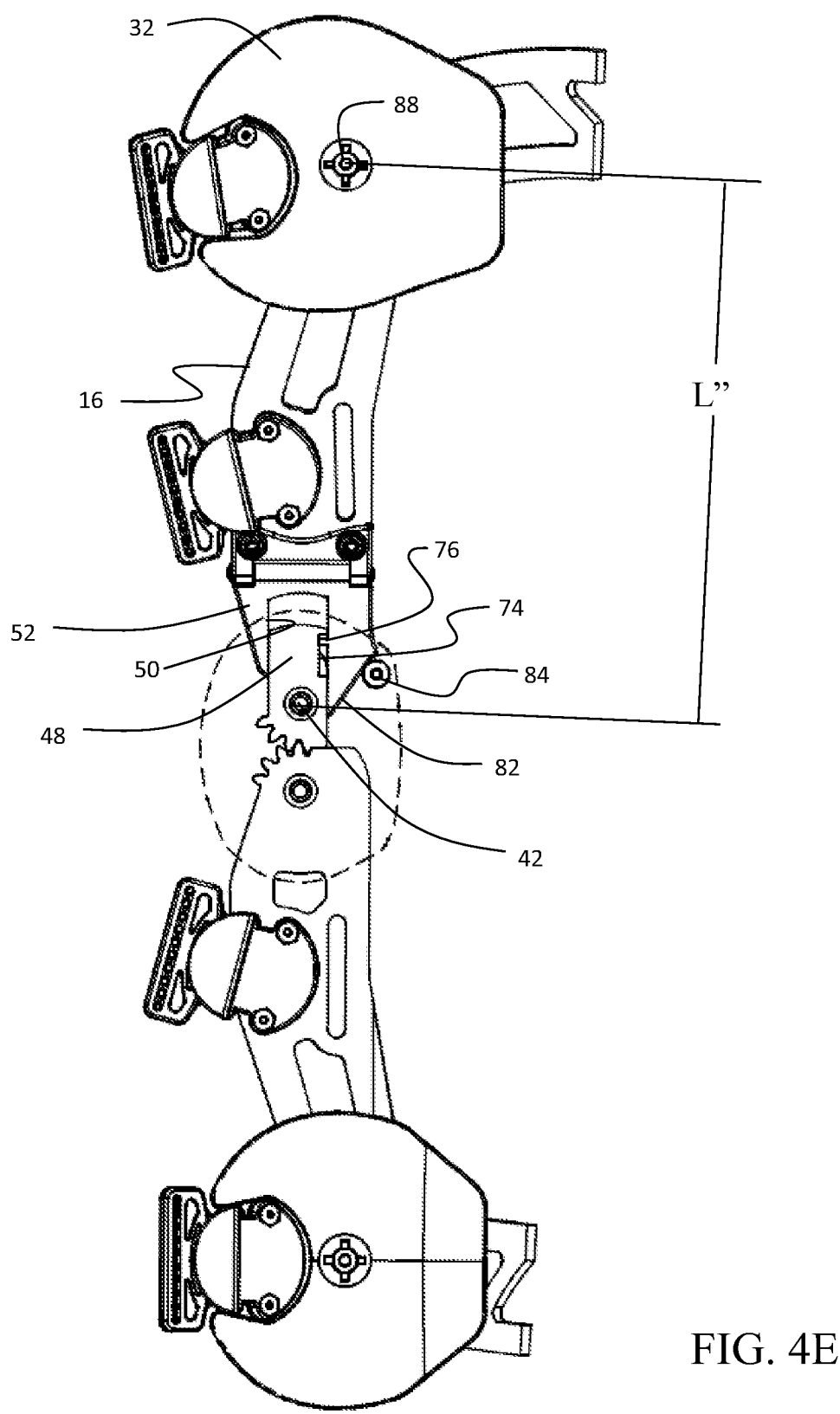
FIG. 4E is a side view of the medial struts of the brace in a fully extended position of the leg with complete dynamic extension.

As seen in FIG. 4B with the brace in a flexed position, buck 48 is substantially fully retracted into channel 50 with the stop pin 76 engaged at the lower termination 80 of relief 74. The ramp 82 is not in contact with the roller 84. In this configuration, the length, L, of the upper medial strut 16, as measured extending from the rotation point 42 to an indicia 88 established at the engagement point of the engagement pad 32, is at a minimum. As the brace is extended from the flexed position and the upper medial strut rotates about the rotation point, a contact point will be reached wherein roller 84 contacts ramp 82 as shown in FIG. 4C. At this point of contact, the buck 48 remains substantially fully retracted and the length, L, of the upper medial strut 16 is not altered. As the brace is further extended, as shown in FIG. 4D, the ramp 82 is urged against the roller 84 urging extension of the buck 48 in channel 50 as the saddle 52 is urged upward. In this configuration, the length, L', of the upper medial strut 16 has extended through approximately one half of the travel of buck 48 relative to saddle 52 with the stop pin 76 approximately mid travel in the relief 74. When the brace reaches a fully extended position as shown in FIG. 4E, engagement of ramp 82 and roller 84 has urged extension of the buck 48 to a fully extended position in the channel 50 relative to the saddle 52. Stop pin 76 has traversed the length of the relief 74 and is engaged at the upper termination 78. In this fully extended position, the length, L", of the upper medial strut 16 is at a maximum. The ramp 82 may be curvilinear to advantageously contact the roller 84 or to alter the rate of extension of the strut versus flexion of the brace. In exemplary embodiments, full travel of the dynamic strut from a fully compressed to a fully extended position may be up to 0.5 inches.

Figure 4F:
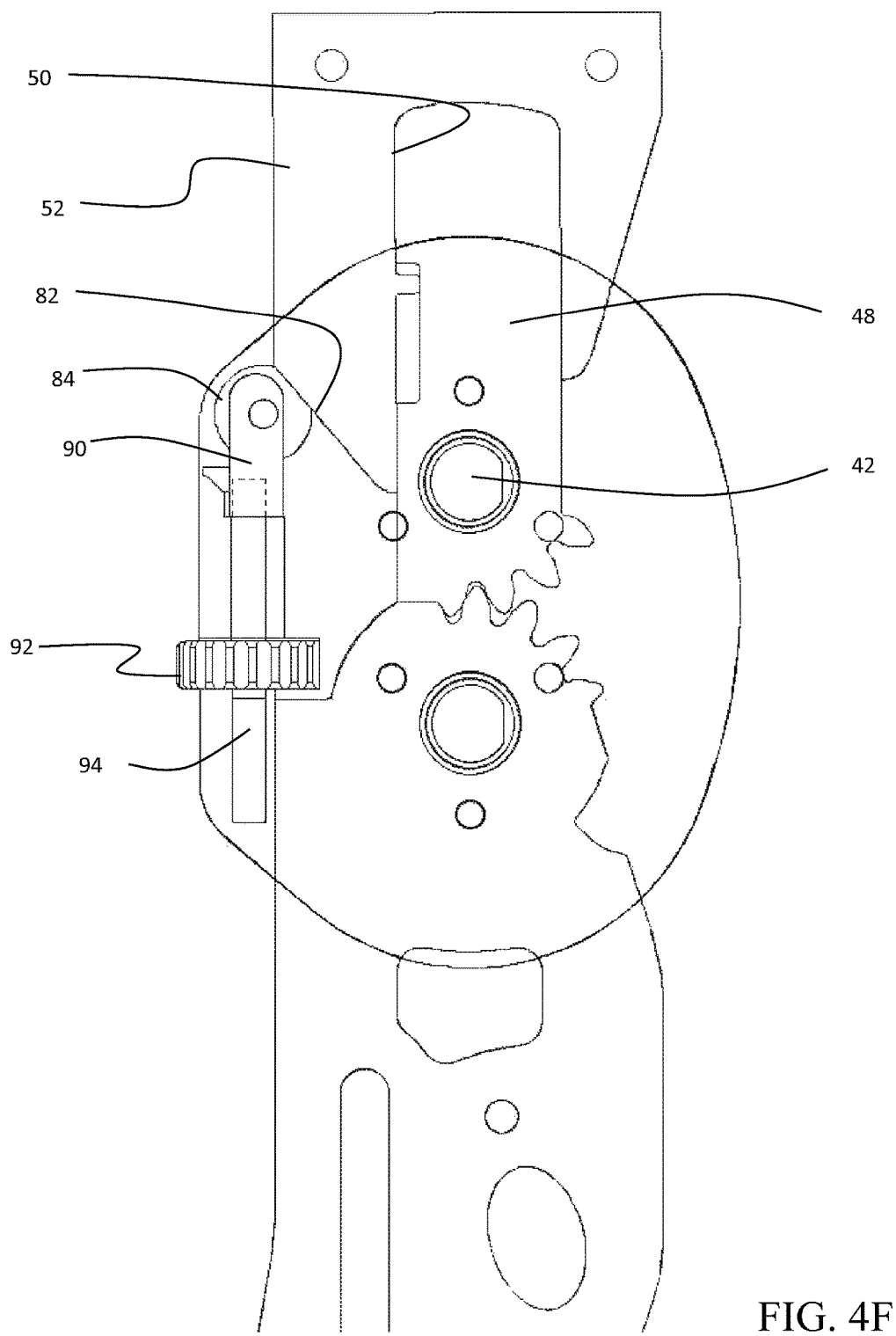
FIG. 4F is a side view of details of an adjustable dynamic extension mechanism.

As the brace is flexed from the fully extended position, a reverse travel of the ramp 82 on the roller 84 and then separation of the ramp from the roller results in contraction of the buck 48 within the channel 50 in a reversal of the described positions for extension. The length of the dynamic extension of the upper medial strut 16 may be altered by adjusting the position of the roller 84 with respect to engagement of the ramp 82. As shown in FIG. 4F, roller 84 may be mounted on a retractable rod 90 with an adjustment wheel 92 rotatable to extend or retract a threaded end 94 on the rod. Retraction of the rod 90 delays contact of the roller 84 and ramp 82 and reduces the amount of relative travel between buck 48 and saddle 52.

Figure 4G:
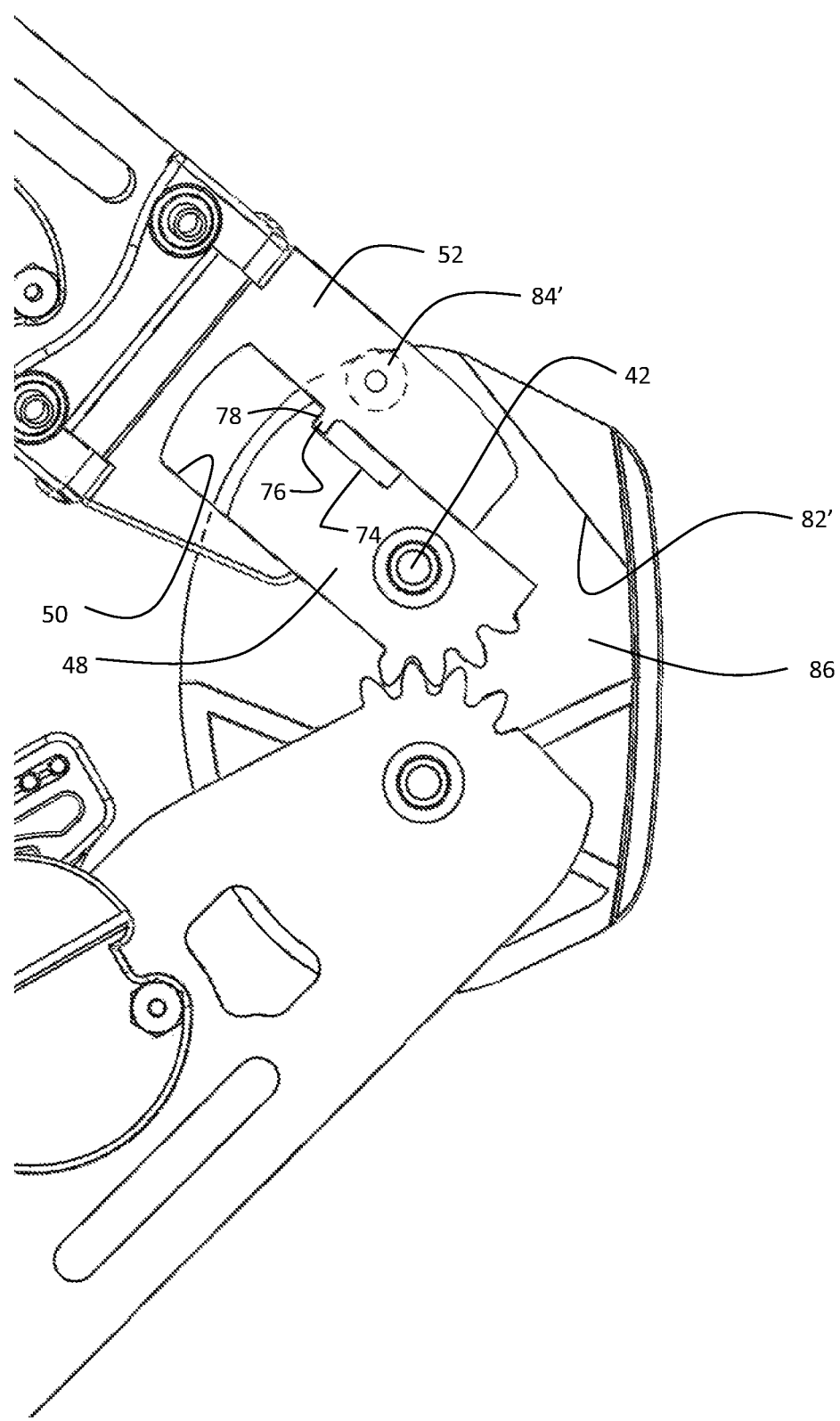
FIG. 4G is a side view in a flexed position of the leg showing details of an alternative dynamic strut with dynamic altering of length by contraction.
Figure 4H:
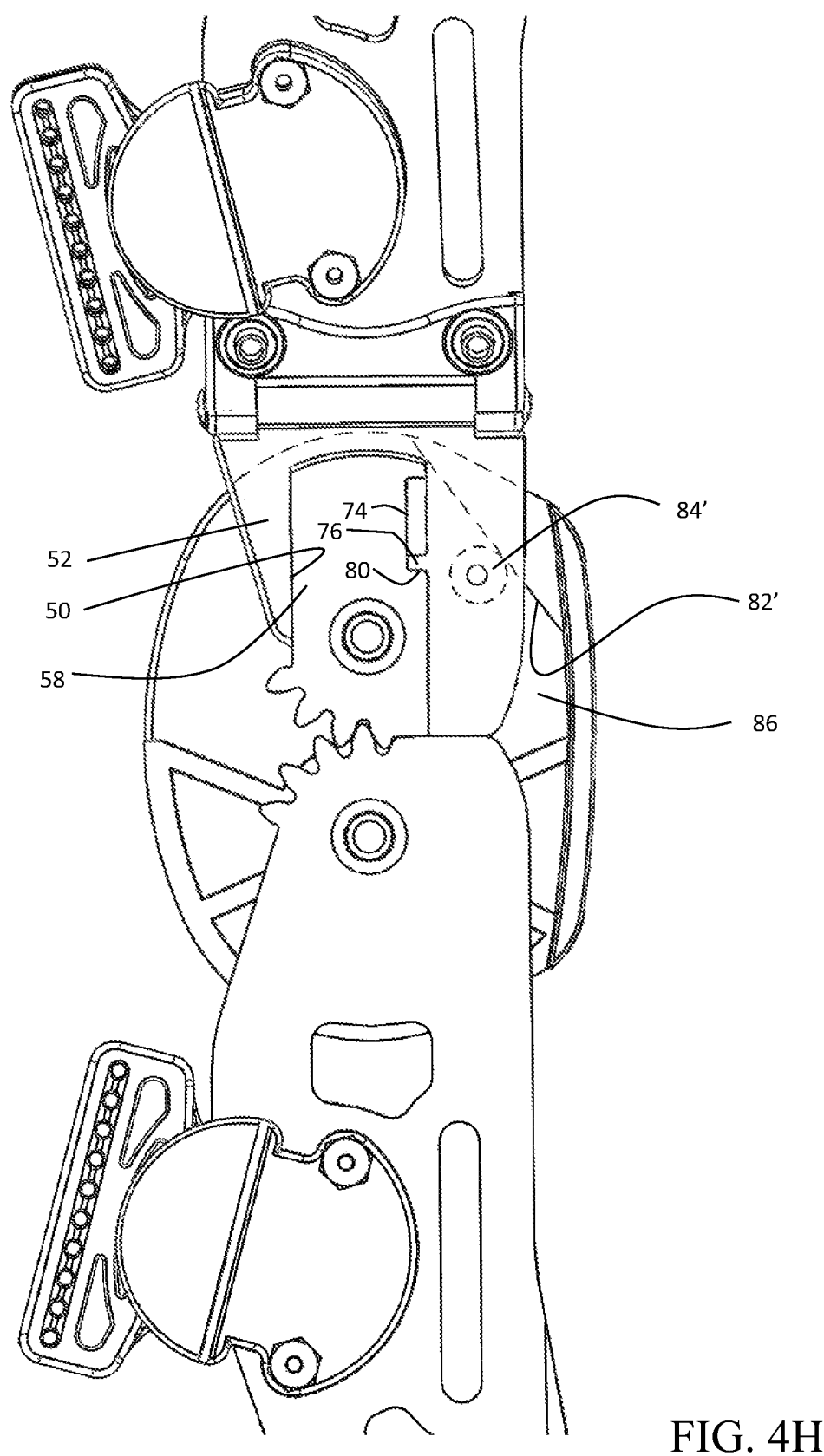
FIG. 4H is a side view in an extended position of the leg of the embodiment of FIG. 4G.

In alternative embodiments, the altering length of the strut may be accomplished by contracting the strut as shown in FIGS. 4G and 4H. As shown in FIG. 4G, with the brace in a flexed position, buck 48 is substantially fully extended in channel 50 with the stop pin 76 engaged at the upper termination 78 of relief 74. A ramp 82' which is integrated with the stationary hinge cover is not in contact with the roller 84' which is mounted to the saddle. In this configuration, the length, L, of the upper medial strut 16, as measured extending from the rotation point 42 to the indicia 88 established at the engagement point of the engagement pad 32, is at a maximum.

As shown in FIG. 4H with the leg in the fully extended position, engagement of ramp 82' and roller 84' has urged contraction of the buck to a fully retracted position in the channel 50 relative to the saddle 52. Stop pin 76 has traversed the length of the relief 74 and is engaged at the lower termination 80. In this fully contracted position, the length, L''', of the upper medial strut 16 is at a minimum. The ramp 82' may be curvilinear to advantageously contact the roller 84' or to alter the rate of contraction of the strut versus flexion of the brace.

Figure 5A:
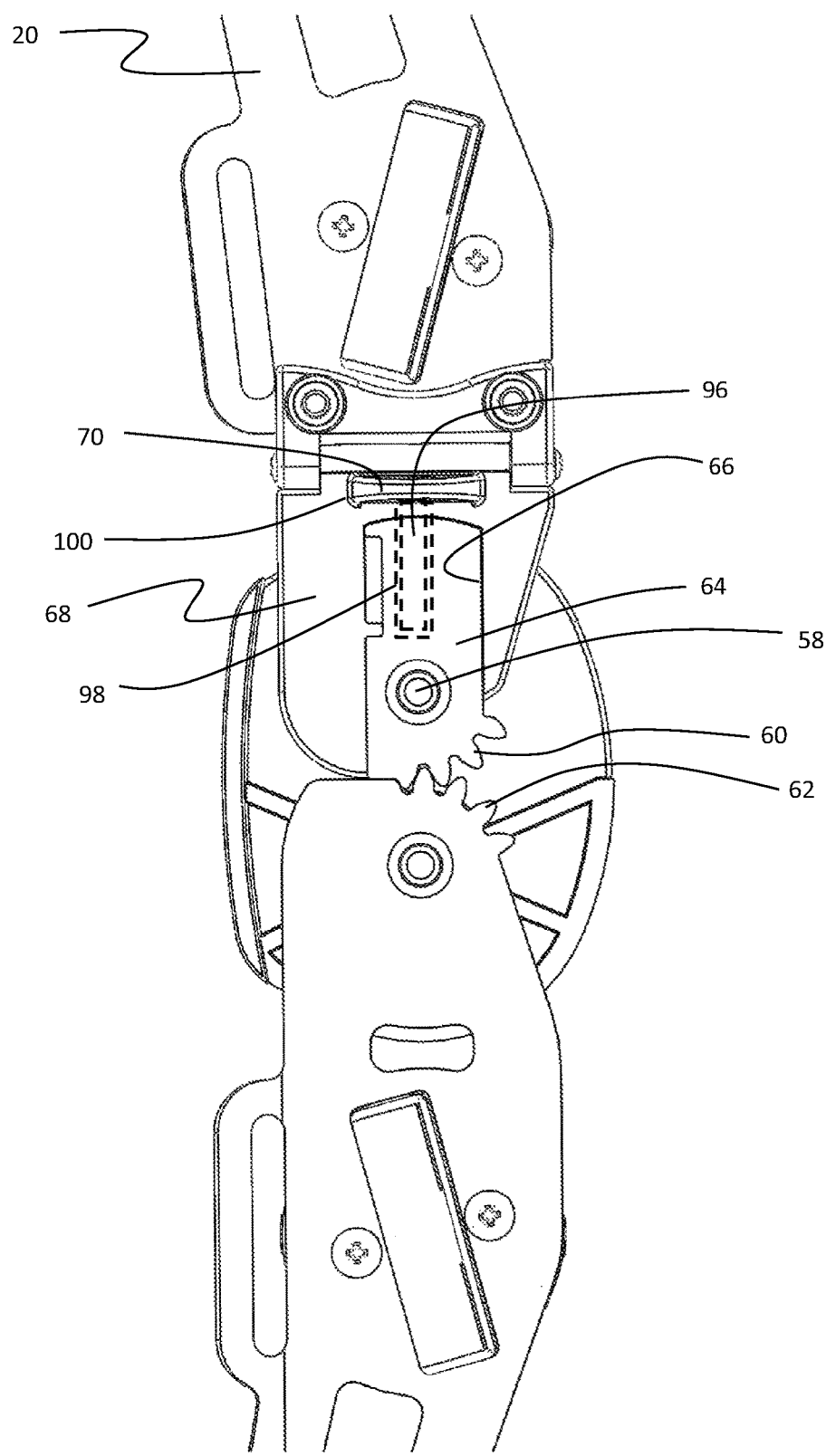
FIG. 5A is a detailed side view of a non-dynamic length adjustment mechanism on the lateral struts of the embodiment adjusted for a minimum length.
Figure 5B:
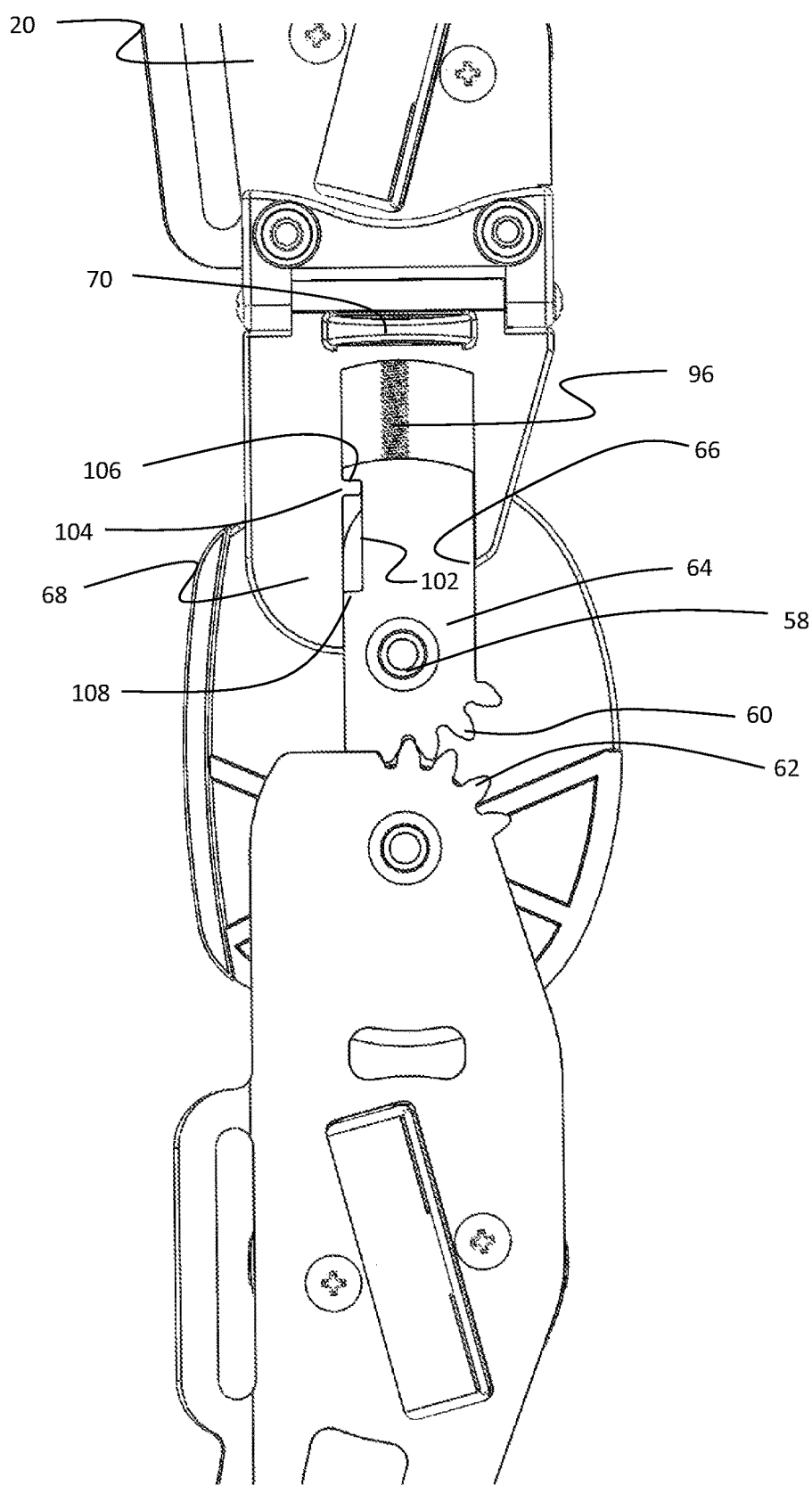
FIG. 5B is a detailed side view of a non-dynamic length adjustment mechanism on the lateral struts of the embodiment adjusted for a maximum length.
Figure 5C:
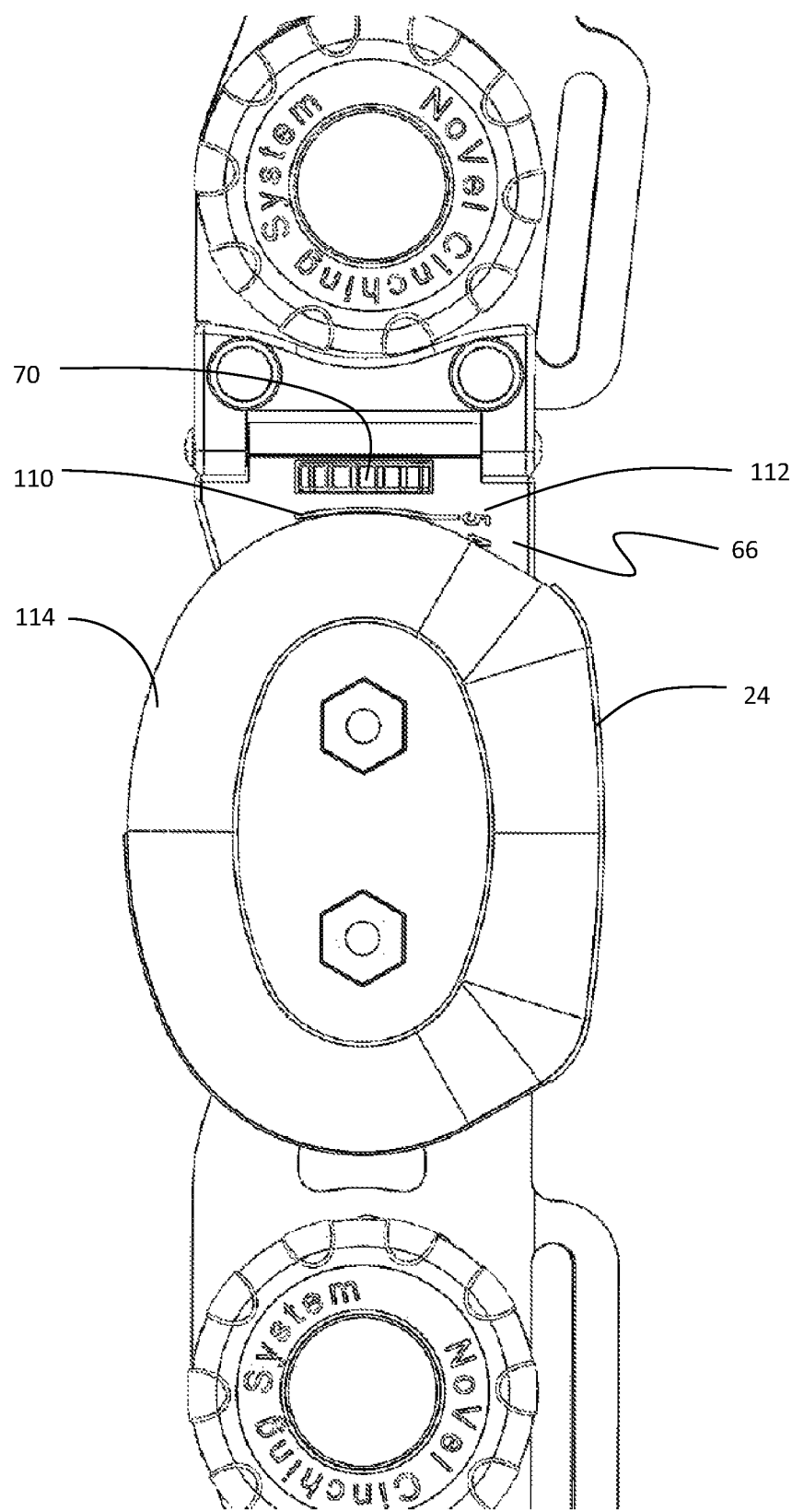
FIG. 5C is a detailed side view of the lateral hinge showing a length measurement indicia for the non-dynamic length adjustment mechanism on the lateral struts of the embodiment adjusted for the minimum length.
Figure 5D:
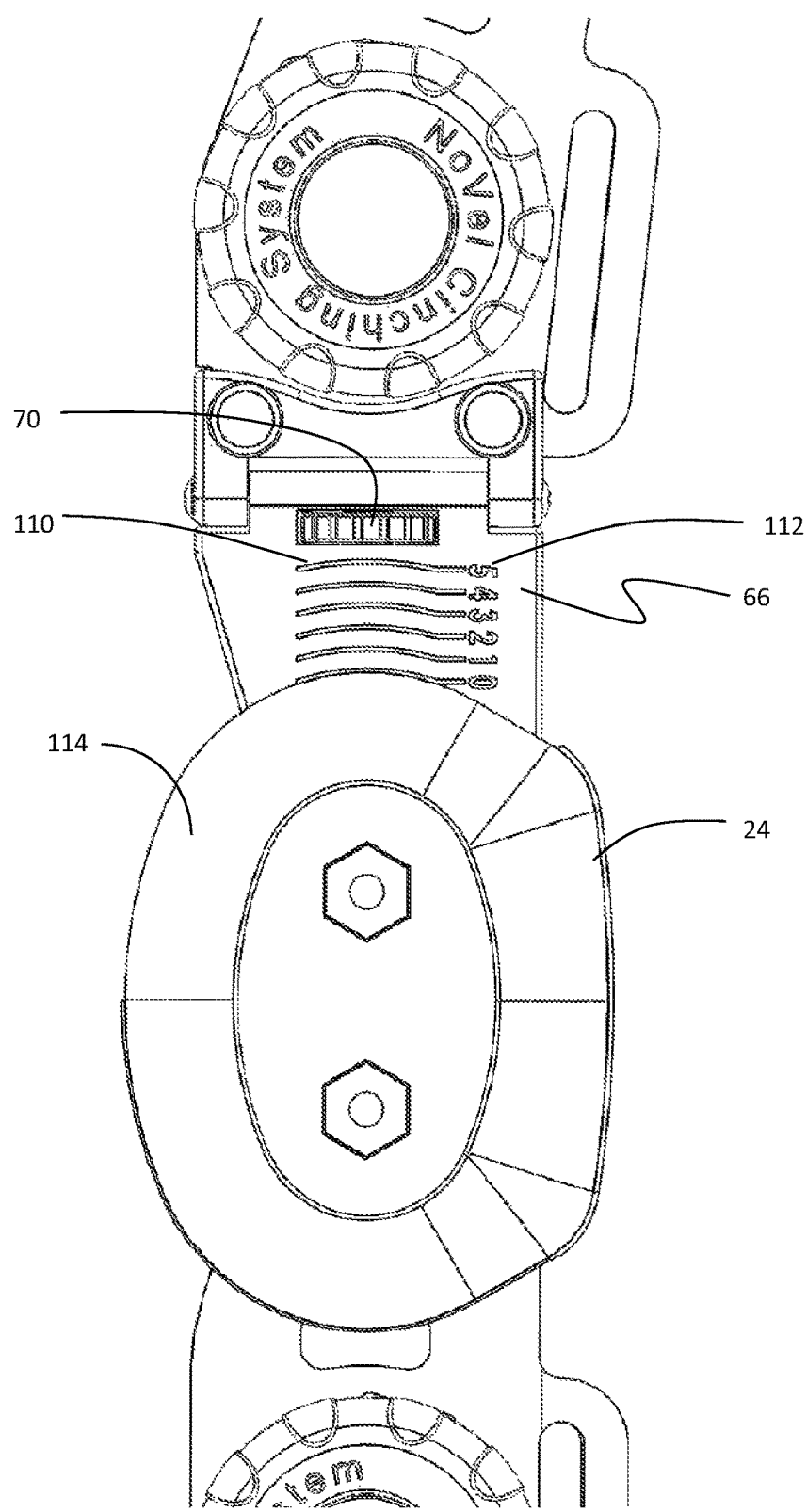
FIG. 5D is a detailed side view of the lateral hinge showing a length measurement indicia for the non-dynamic length adjustment mechanism on the lateral struts of the embodiment adjusted for the maximum length.

As shown in detail in FIGS. 5A-5D, non-dynamic adjustment of the length of the upper lateral strut 20 is accomplished by adjustment of the buck 64 within the channel 66 in saddle 68. A threaded rod 96 extends from the adjustment wheel 70 to be received in a threaded bore 98 in the buck 64. Adjustment wheel 70 is constrained in a pocket 100 in the saddle and rotation of the wheel results in extension or retraction of the buck 64 in the channel 66. FIG. 5A shows the buck 64 in a fully retracted position. FIG. 5B shows the buck 64 in a fully extended position A relief 102 in the buck 64 engages a stop pin 104 extending from the saddle 68 which restricts travel of the buck by contacting an upper termination 106 of the relief 102 in the fully extended position and a lower termination 108 of the relief 102 in a fully retracted position. Indices for measurement of the length of extension may be provided as shown in FIGS. 5C and 5D. Graduated lines 110 with associated numerical indicators 112 are provided on the saddle 68. A top edge of case 114 of hinge 24 provides a visual indication of the amount of extension by alignment with the graduated lines 110.

Figure 6:
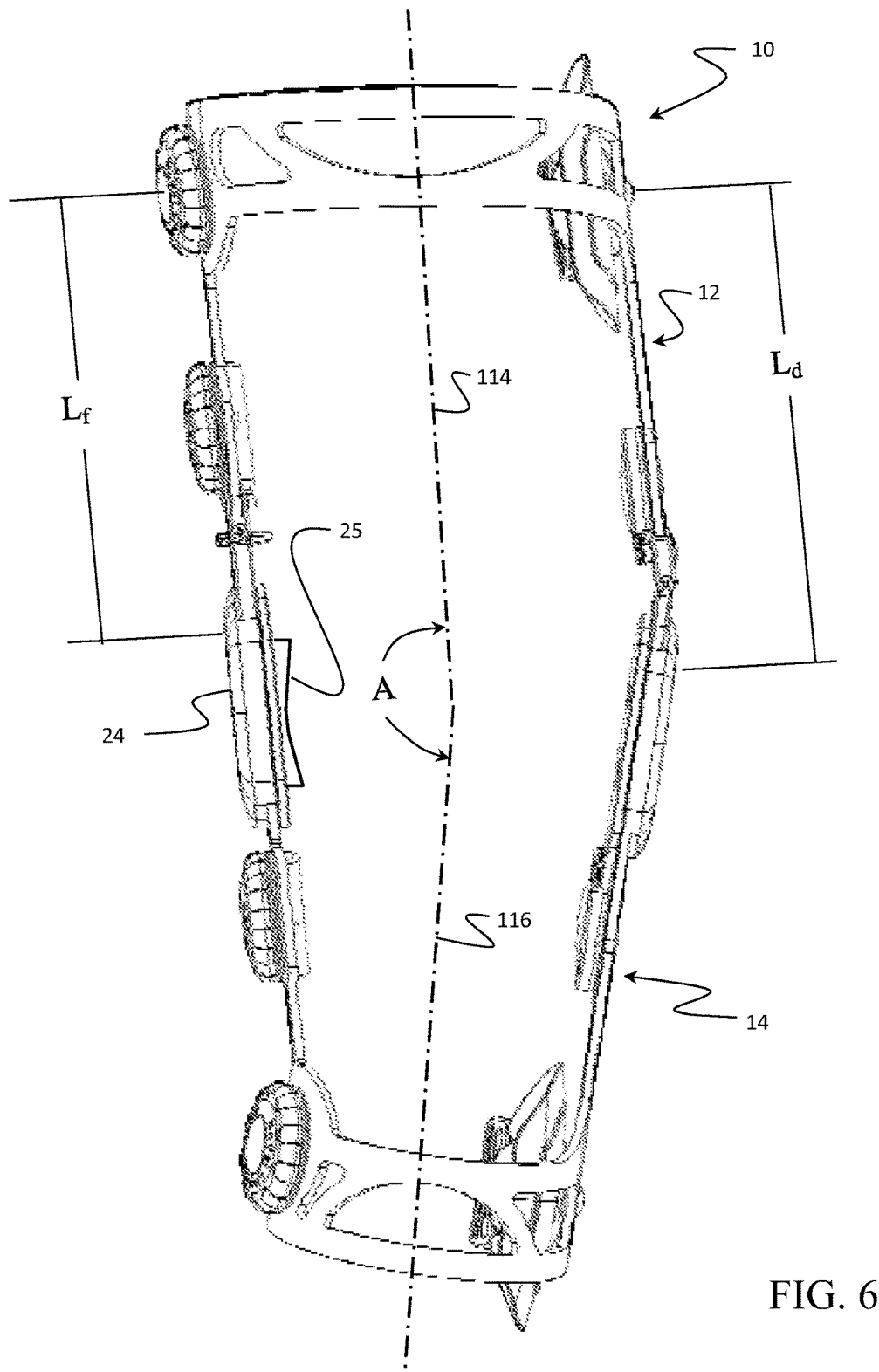
FIG. 6 is a front view of the brace demonstrating the angular relationship of the upper attachment assembly and lower attachment assembly.

Action of the brace 10 to impart anatomical adjustments for the user is demonstrated in FIG. 6. A nominal axis 114 of the upper attachment assembly 12 and nominal axis 116 of the lower attachment assembly 14 meet with an angle A. The dynamic lengthening (or, in alternative embodiments, contracting) of the length, Ld, of the medial strut of the upper attachment assembly relative to the fixed length Lf of the lateral strut of the upper attachment assembly during motion of the brace from the flexed to extended position of the leg urges a change in angle A or, alternatively, application of a medial to lateral force at the knee joint exerted through the upper cuff 28 and upper medial pad 32 acting on the upper leg or thigh of the user and the lower cuff 30 and lower medial pad 34 acting on the lower leg with reaction force at the knee at the hinge 24, which may have a pad 25 attached, which unloads the medial portions of the knee joint in the extended position. The relative angular or force change may be adjusted by either the dynamic extension adjustment described with respect to FIG. 4F or the non-dynamic adjustment as described with respect to FIGS. 5A and B.

Figure 7:
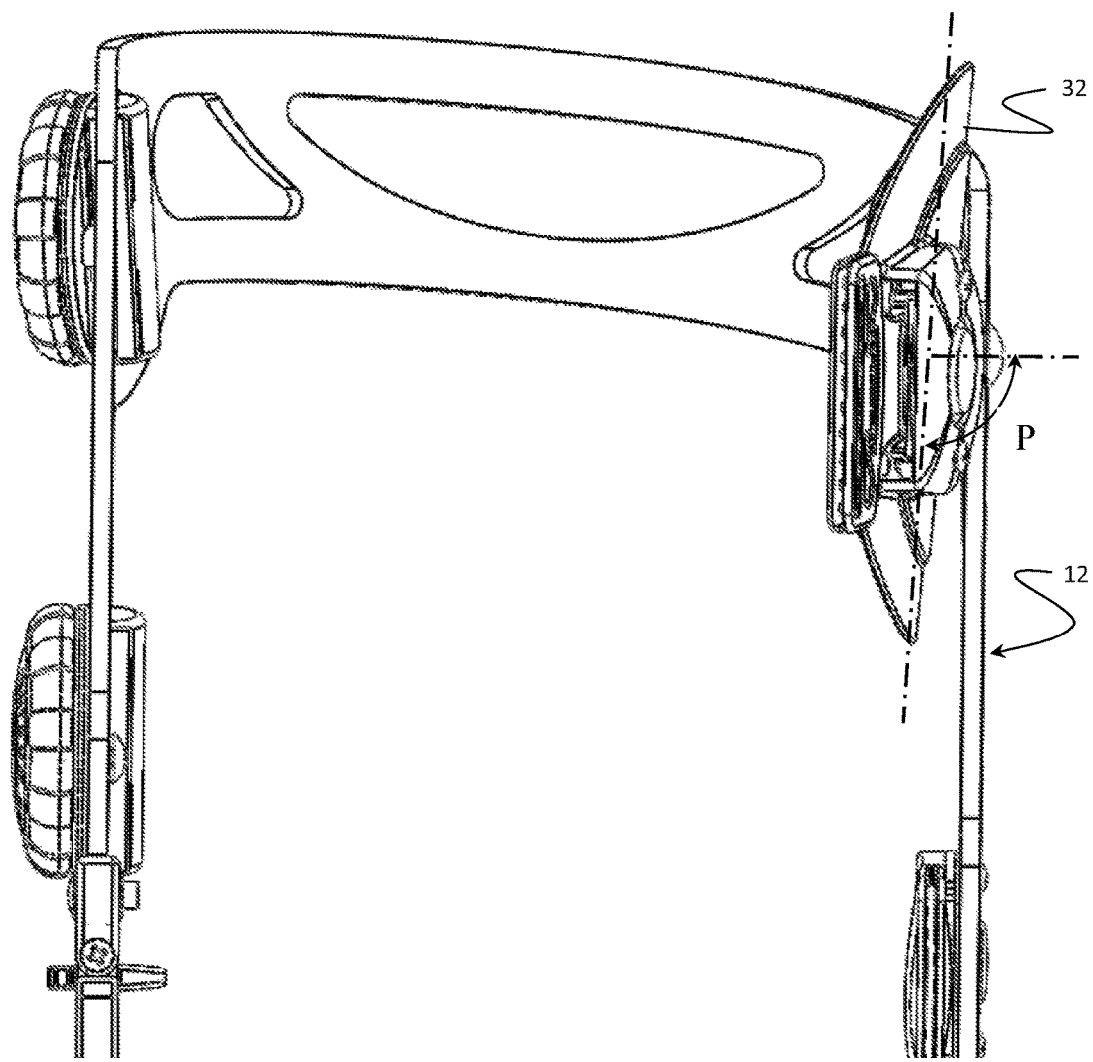
FIG. 7 is a detailed rear view of the upper attachment assembly with the upper pad at a first angle; and, FIG. 8 is a detailed rear view of the upper attachment assembly with the upper pad at a second angle.
Figure 8:
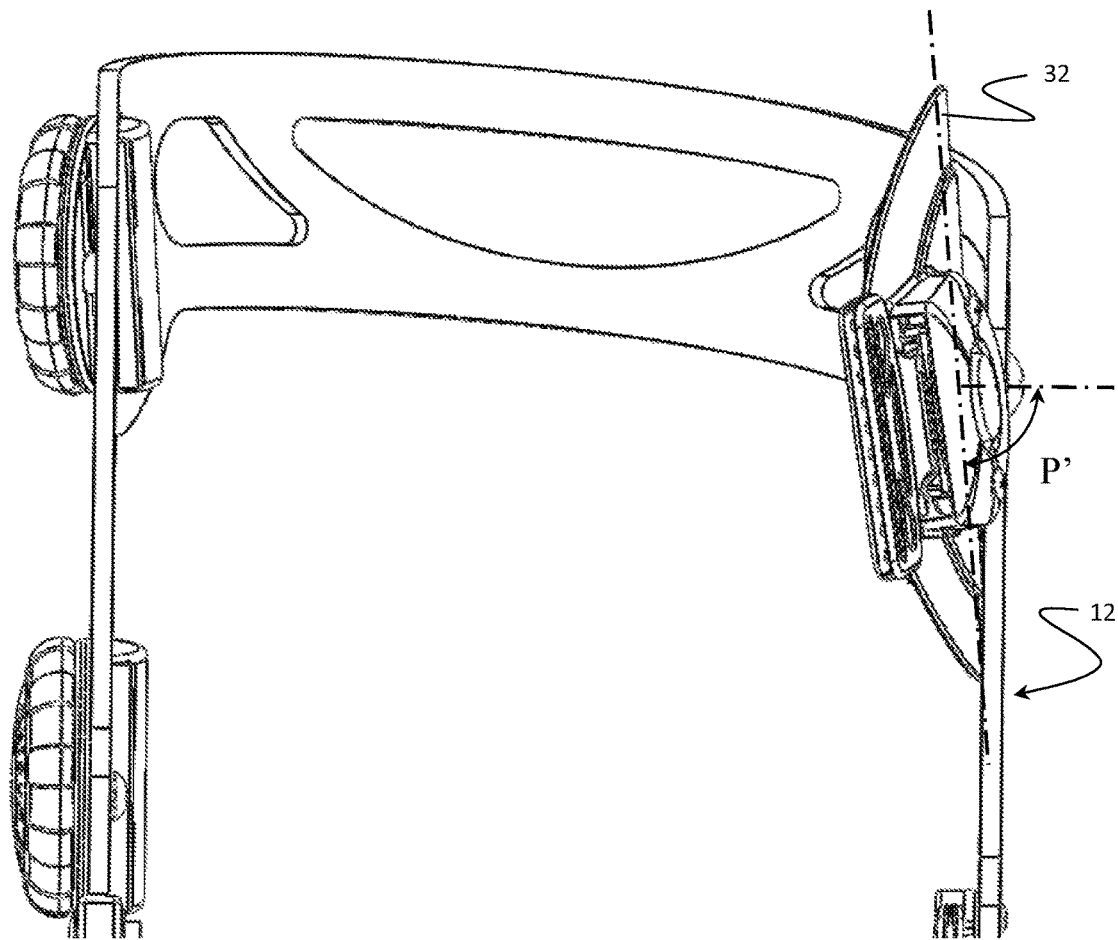

The upper and lower medial pads 32, 34 are mounted to the upper and lower medial struts 16, 18 with a multidirectional joint such as a ball and socket arrangement or a rod and spherical bearing attachment to be angularly compliant (angularly displaceable in any angular direction) with respect to the struts on which they are mounted. This provides angular relief for the upper and lower attachment assemblies of the brace and the leg and shown in FIGS. 1 and 8. Angle P of the upper pad 32 with a first loading as shown in FIG. 7 alters to a revised angle, P', for upper pad 32 under a second loading as shown in FIG. 8 (exaggerated for clarity) thereby allowing the brace to induce the necessary relative forces without undesired torsional strain imparted by the brace on the leg. The lower pad 34 rotates similarly for alignment of the lower medial strut. The brace extension may result in medial or lateral unloading. The embodiment shown in the drawings is for a right leg medial unloader. The pads 32, 34 may be located on the lateral struts and pad 25 shown in FIG. 6 moved to the medial hinge cover to accommodate lateral unloading.

While the embodiments described herein have shown the dynamic strut on the medial side of the brace and the non-dynamic length adjustment on the lateral side for medial unloading of a right leg, alternative embodiments may employ those functions on the opposite sides for lateral unloading and also as fitted with either option for the left leg. Similarly while the embodiments have been described with the operating elements for lengthening or contracting on the upper struts, operating elements for lengthening and contracting may be employed on the lower struts or may be employed in combination on both upper and lower struts. Directional terms upward and downward and upper and lower have been used with respect to descriptions as related to the drawings but have no limiting effect except to provide relative positioning between elements of the embodiments described.

Having now described various embodiments of the disclosure in detail as required by the patent statutes, those skilled in the art will recognize modifications and substitutions to the specific embodiments disclosed herein. Such modifications are within the scope and intent of the present disclosure as defined in the following claims.

What is claimed is:

1. A knee brace comprising:
   an upper attachment assembly having an upper cuff with an upper medial strut and an upper lateral strut extending therefrom;
   a lower attachment assembly having a lower cuff with lower medial strut and a lower lateral strut extending therefrom, said upper and lower medial struts configured to be connected proximate a user's knee by an associated medial hinge assembly, said upper medial strut rotatable about a first rotation point and said lower medial strut rotatable about a second rotation point, said upper and lower lateral struts configured to be connected proximate the user's knee by an associated lateral hinge assembly, said upper lateral strut rotatable about a third rotation point and said lower lateral strut rotatable about a fourth rotation point, wherein
   at least one of said upper medial strut, upper lateral strut, lower medial strut or lower lateral strut having a mechanism dynamically altering a length of said at least one of said upper medial strut, upper lateral strut, lower medial strut or lower lateral strut, with respect to an associated one of the first, second, third or fourth rotation points in the associated medial or lateral hinge assembly upon flexion of the upper and lower attachment assemblies between a flexed position and an extended position, said mechanism comprising a buck directly connected to a pivot pin at the associated one of the first, second, third or fourth rotation point;

a saddle directly connected to an interface in the at least one strut and having a channel receiving the buck for reciprocal motion through a range from a contracted position to an extended position; and, a roller fixed in one of the associated hinge assembly or the saddle offset from the associated one of the first, second, third or fourth rotation point, and a ramp on a periphery of the saddle or fixed in the associated hinge assembly said roller contacting the ramp during flexion of the upper and lower attachment assemblies between the flexed position and the extended position to urge the saddle from the contracted position to the extended position.

2. The knee brace of claim 1 wherein at least a second one of said upper medial strut, upper lateral strut, lower medial strut or lower lateral strut has a second mechanism to non-dynamically adjust the length of the at least a second one of said upper medial strut, upper lateral strut, lower medial strut or lower lateral strut.

3. The knee brace of claim 2 wherein the second mechanism comprises:

a second buck connected to a second rotation pin at an associated second one of the first, second third or fourth rotation point;

a second saddle connected to a second interface in the at least the second one of said upper medial strut, upper lateral strut, lower medial strut or lower lateral strut and having a second channel receiving the second buck for adjustable motion through a range from a retracted position to an extended position; and, a threaded rod received in a threaded bore in the second buck, said threaded rod rotatable by an adjustment knob to extend or retract the second buck in the second channel in the second saddle.

4. The knee brace of claim 3 wherein the second saddle is attached to the second interface in the at least one second one of said upper medial strut, upper lateral strut, lower medial strut or lower lateral strut by a second hinge.

5. The knee brace of claim 1 wherein said saddle periphery has the ramp; and, the roller is fixed in the associated medial or lateral hinge assembly.

6. The knee brace of claim 5 wherein the roller is adjustable to change a length between the contracted and extended positions of the buck and saddle.

7. The knee brace of claim 5 wherein the saddle is attached to the interface in the at least one of said upper medial strut, upper lateral strut, lower medial strut or lower lateral strut by a hinge.

8. The knee brace of claim 1 further comprising:

an upper medial pad attached to the upper medial strut proximate the upper cuff, said upper medial pad angularly compliant with respect to said upper medial strut.

9. The knee brace of claim 1 further comprising:

a lower medial pad attached to the lower medial strut proximate the lower cuff, said lower medial pad angularly compliant with respect to said lower medial strut.

10. A knee brace comprising:

an upper attachment assembly having an upper cuff with an upper medial strut extending therefrom;

a lower attachment assembly having a lower cuff a with lower medial strut extending therefrom, said upper and lower medial struts configured to be connected proximate a user's knee by an associated medial hinge assembly, said upper medial strut rotatable about a first rotation point in the medial hinge assembly and the lower medial strut rotatable about a second rotation point the medial hinge assembly wherein said upper medial strut includes a mechanism dynamically altering a length of said upper medial strut with respect to the first rotation point in the associated medial hinge assembly upon flexion of the upper and lower attachment assemblies between a flexed position and an extended position, said mechanism comprising a buck directly connected to a pivot pin at the first rotation point;

a saddle directly connected to an interface in the upper medial strut and having a channel receiving the buck for reciprocal motion through a range from a contracted position to an extended position; and, a roller fixed in the medial hinge assembly and a ramp on a periphery of the saddle, said roller contacting the ramp during flexion of the upper and lower attachment assemblies between the flexed position and the extended position to urge the saddle from the contracted position to the extended position.

11. The knee brace as defined in claim 10 wherein the upper cuff has an upper lateral strut attached thereto and the lower cuff has a lower lateral strut attached thereto, said lower medial strut rotatable about a second rotation point in the medial hinge assembly, said upper and lower lateral struts configured to be connected proximate the user's knee by an associated lateral hinge assembly, said upper lateral strut rotatable about a third rotation point in the lateral hinge assembly and said lower lateral strut rotatable about a fourth rotation point in the lateral hinge assembly and the upper lateral strut, has a second mechanism to non-dynamically adjust the length of the upper lateral strut, the second mechanism comprising:

a second buck connected to a second rotation pin at the third rotation point;

a second saddle connected to a second interface in the upper lateral strut having a second channel receiving the second buck for adjustable motion through a range from a retracted position to an extended position; and, a threaded rod received in a threaded bore in the second buck, said threaded rod rotatable by an adjustment knob to extend or retract the second buck in the second channel in the second saddle.

* * * * *